US007365320B2

(12) United States Patent
Shemesh

(10) Patent No.: US 7,365,320 B2
(45) Date of Patent: Apr. 29, 2008

(54) METHODS AND SYSTEMS FOR PROCESS MONITORING USING X-RAY EMISSION

(75) Inventor: Dror Shemesh, Petah Tikva (IL)

(73) Assignee: Applied Materials Israel, Ltd., Rehovot (IL)

( * ) Notice: Subject to any disclaimer, the term of this patent is extended or adjusted under 35 U.S.C. 154(b) by 307 days.

(21) Appl. No.: 10/530,178

(22) PCT Filed: Oct. 8, 2003

(86) PCT No.: PCT/US03/31998

§ 371 (c)(1),
(2), (4) Date: Sep. 12, 2005

(87) PCT Pub. No.: WO2004/034043

PCT Pub. Date: Apr. 22, 2004

(65) Prior Publication Data

US 2006/0054811 A1    Mar. 16, 2006

Related U.S. Application Data

(60) Provisional application No. 60/417,273, filed on Oct. 8, 2002.

(51) Int. Cl.
*H01J 37/153* (2006.01)
*G01N 23/00* (2006.01)
*G21K 7/00* (2006.01)

(52) U.S. Cl. ..................... 250/310; 250/307; 250/306; 250/305; 250/492.2; 250/492.1

(58) Field of Classification Search ...................... None
See application file for complete search history.

(56) References Cited

U.S. PATENT DOCUMENTS

| 4,857,731 A | 8/1989 | Tagata |
| 5,801,382 A | 9/1998 | Noda et al. |
| 7,205,555 B2 * | 4/2007 | Okuda et al. ............ 250/492.2 |

FOREIGN PATENT DOCUMENTS

| EP | 0 377 446 A | 7/1990 |
| WO | WO 01 44794 A | 6/2001 |

OTHER PUBLICATIONS

International Search Report, PCT/US2003/031998, Mar. 18, 2004, 5pp.
Willich, P., Bethke, R., Performance and limitations of electron probe microanalysis applied to the characterization of coatings and layered structures, Jan. 16, 1995, 4pp.

* cited by examiner

*Primary Examiner*—Jack I. Berman
*Assistant Examiner*—Zia R. Hashmi
(74) *Attorney, Agent, or Firm*—Tarek N. Fahmi

(57) ABSTRACT

Systems and methods for process monitoring based upon X-ray emission induced by a beam of charged particles such as electrons or ions include a system and method for process monitoring that analyze a cavity before being filled and then analyze emitted X-rays from the cavity after the cavity has been filled with a conductive material. Also included are system and methods for process monitoring that apply a quantitative analysis correction technique on detected X-ray emissions.

52 Claims, 11 Drawing Sheets

Target 75
(scanning window)

Target 77
(scanning window)

|  | White - seventh range of copper voids volume |  | Brown - fourth range of copper voids volume |
| --- | --- | --- | --- |
|  | Blue - sixth range of copper voids volume |  | Purple - third range of copper voids volume |
|  | Yellow - fifth range of copper voids volume |  | Green - second range of copper voids volume |
| | |  | Red - first range of copper voids volume |

METHODS AND SYSTEMS FOR PROCESS MONITORING USING X-RAY EMISSION

CROSS-REFERENCES TO RELATED APPLICATIONS

The present patent application is a national phase application of International Application No. PCT/US03/031998 filed Oct. 8, 2003, which claims priority from U.S. Provisional Application No. 60/417,273 filed Oct. 8, 2002.

FIELD OF THE INVENTION

The invention relates to scanning electron microscopes and especially to a measurements of copper layer thickness and detection of voids.

BACKGROUND OF THE INVENTION

Integrated circuits are very complex devices that include multiple layers. Each layer may include conductive material and/or isolating material while other layers may include semi-conductive materials. These various materials are arranged in patterns, usually in accordance with the expected functionality of the integrated circuit. The patterns also reflect the manufacturing process of the integrated circuits.

Integrated circuits are manufactured by complex multi-staged manufacturing processes. This process may include depositing photo-resistive material on a substrate or layer, selectively exposing the resistive material by a photolithographic process, and developing the photo-resistive material to produce a pattern that defines some areas to be later etched or otherwise processed. After the pattern is processed various materials, such as copper are disposed. The deposition step is usually followed by a removing access material, such as chemical mechanical polishing (CMP). The polishing can result in various deformation, such as dishing and erosion.

Various metrology, inspection and failure analysis techniques evolved for inspecting integrated circuits both during the manufacturing stages, between consecutive manufacturing stages, either in combination with the manufacturing process (also termed "in line" inspection techniques) or not (also termed "off line" inspection techniques). It is known that manufacturing failures may affect the electrical characteristics of the integrated circuits. Some of these failures result from unwanted deviations from the required dimensions of the patterns.

X-ray reflectivity (XRR) and X-ray florescence (XRF) are methods that use X-rays to determine the thickness of thin films. Various vendors sell metrology tools that utilize these methods for thin film thickness determination. One of these vendors is Jordan Valley Ltd. of Israel that sells various tools. The JVX5200 metrology tool implements both methods.

These X-ray based methods can also be utilized for detection of voids within thin films. A brief description of the state of the art may be found in the following patents and patent applications, all being incorporated herein by reference: U.S. Pat. No. 6,556,652 titled "Measurement of critical dimensions using X-ray" of Mazor et al., U.S. Pat. No. 6,535,575 titled "Pulsed X-ray reflectometer" of Yokhin, U.S. Pat. No. 6,041,095 titled "X-ray fluorescence analyzer" of Yokhin, U.S. Pat. No. 6,389,102 titled "X-ray array detector" of Mazor et al., U.S. patent application Ser. No. 2003/0156682 titled "Dual-wavelength X-ray reflectometry" of Yokhin et al.

X-ray spot is relatively large. For example, the JVX5200 tool can produce a spot of about 18-30 micron when implementing XRF, and a larger spot (due to grazing angle illumination) that has a length of about 2-8 millimeters when implementing XRR. These measurements require relatively large test pads (about 70×100 micron for XRF and 100-150×2000-5000 microns for XRR).

Electron beam metrology and defect detection tools, such as Scanning Electron Microscopes are used for high resolution measurement of surface features as well as surface defects and contaminations. These tools generate a spot of electrons that is very small. Typical spots may have a length of about few nanometers. These electron beam metrology and defect detection tools are not able to detect voids or measure the thickness of layers, such as oblique layers and especially of copper layers.

U.S. patent application Ser. Nos. 10/242,496, 09/990,170 and 09/990,171 of Nasser-Ghodsi et el. titled respectively, "Methods and system for dishing and erosion characterization", "Methods and system for defect localization" and "methods and system for void characterization" also provide a description of prior art methods and systems for analyzing copper films.

U.S. patent application Ser. No. 09/990,171 of Nasser-Ghodsi describes a system and method that provides an indication about the presence of voices in response to the measurement counts. It is noted that said count based system and method are prone to various errors resulting from measurement inaccuracies, such as difference between measurements, different X-ray absorption and emission characteristics by different materials.

SUMMARY OF THE INVENTION

In various embodiments, the invention provides systems and methods for process monitoring based upon X-ray emission induced by a beam of charged particles such as electrons or ions.

In further embodiments, the invention provides a system and method for process monitoring that analyze a cavity before the cavity is filled and then analyzing emitted X-rays from the cavity after the cavity has been filled with a conductive material.

In yet other embodiments, the invention provides a system and method for process monitoring that apply quantitative iterative analysis correction technique on detected X-ray emissions.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION

The invention relates to systems and methods for process monitoring and for detecting voids in thin layers, and additionally or alternatively, for determining the thickness of thin opaque layers.

Figure 1:
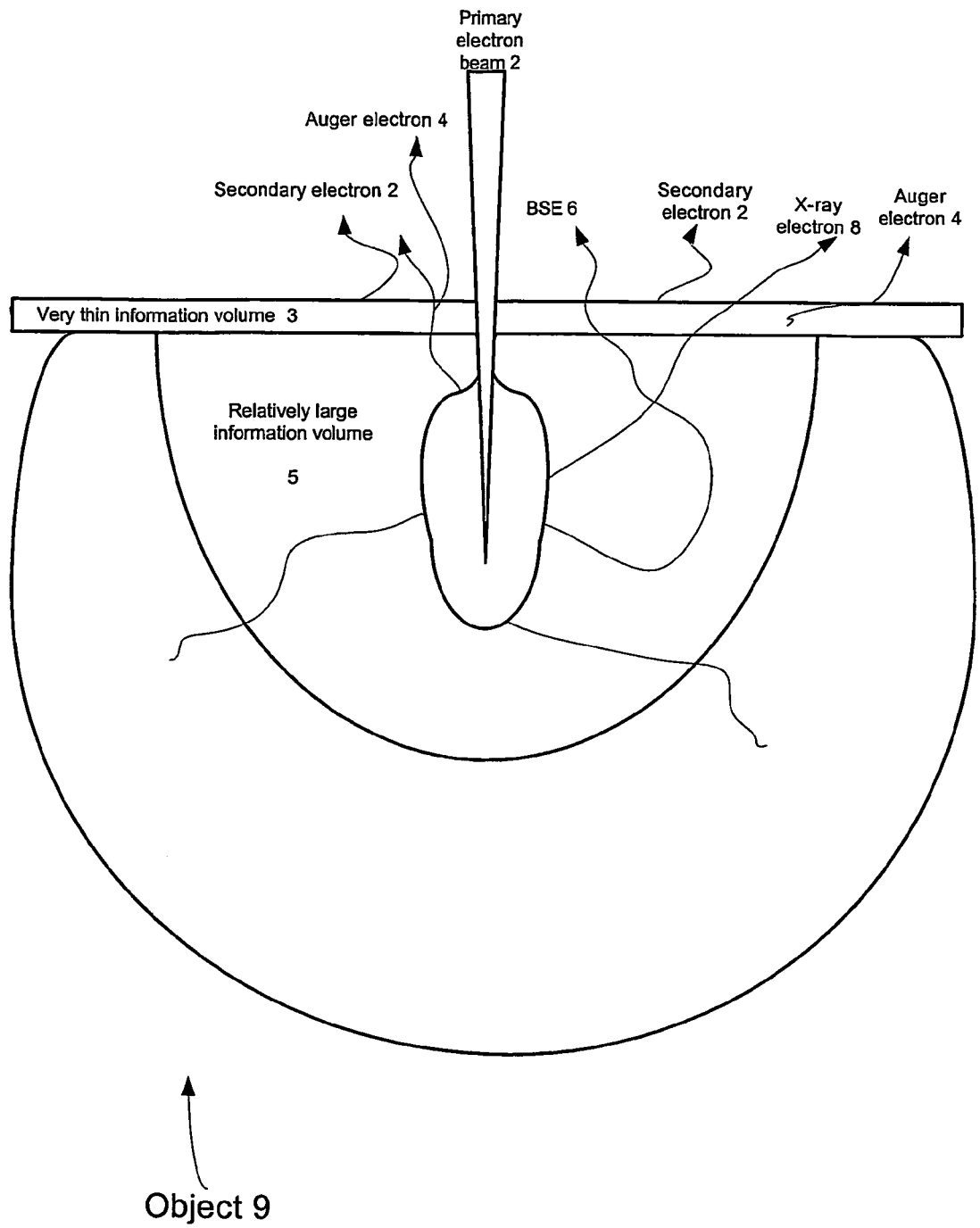
FIG. 1 illustrates interaction process between a sample and a beam of charged particles as well as various information volumes.

FIG. 1 illustrates various interaction process and various information volumes. An information volume is a space in which an interaction process occurs and result in an emission of X-rays or electrons that may be eventually detected to provide information about the information volume.

The figure illustrates a primary electron beam 2 that hits a sample 20 at an interaction point 11. As a result, secondary electrons 2 and Auger electrons 4 are emitted from a very thin information volume 3 while back scattered electrons (USE) 6 and X-ray 8 can leave the inspected object from a relatively large information volume 5 that has a depth that may even exceed one micron.

It is noted that the distribution of electrons within the relatively large information volume 5 is not homogenous. The flux of electrons decreases at longer distance from interaction point 11.

An indication about a depth of a void may be detected by illuminating the vicinity of the void by beams of different energies.

Figure 2:
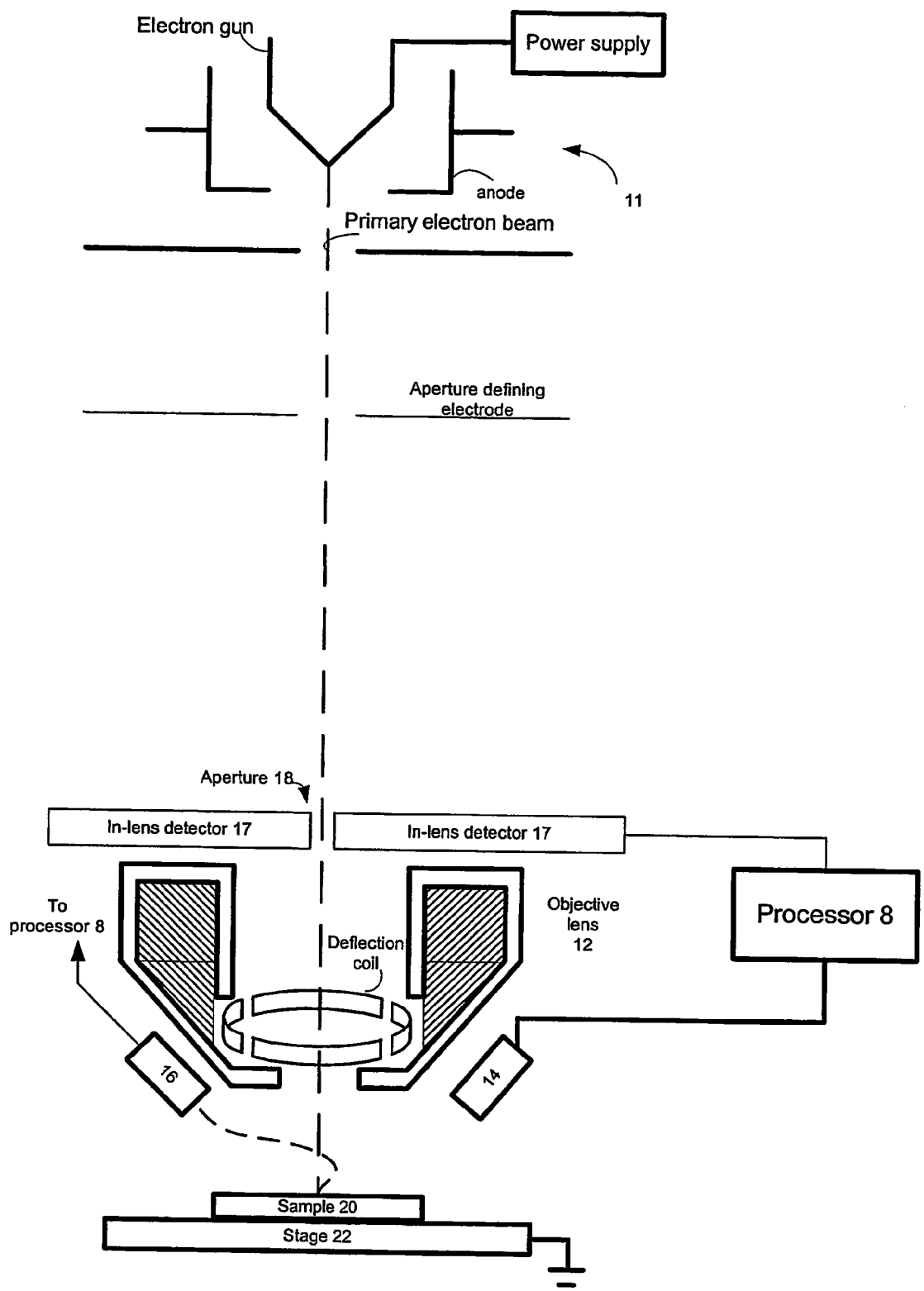
FIG. 2 illustrates a Scanning Electron Microscope (SEM) that may be used for process monitoring, according to an embodiment of the invention.

FIG. 2 illustrates a Scanning Electron Microscope (SEM) 10 that may be utilized for process monitoring, according to an embodiment of the invention. SEM 10 includes an electron gun (not shown) for generating a primary electron beam, as well as multiple control and voltage supply units (denoted 11), an objective lens 12, and an EDX detector 14.

It is noted that SEM 10 may include more than a single detector. SEM 10 may include at least one detector positioned in-lens (like optional secondary electron detector 16), and/or at least one external detector (such as EDX detector 14). SEM 10 may include detectors of various types, such as a secondary electron detector, a backscattered electron detector, a narrowband X-ray detector, and the like. Each detector can include a single sensing element, or may include an array of sensing elements. The detectors may be positioned to detect radiation emitted towards different directions.

In SEM 10 the primary electron beam is directed through an aperture 18 within the optional in-lens detector 17 to be focused by the objective lens 12 onto an inspected sample 20. The primary electron beam interacts with sample 20 and as a result various types of electrons and photons, such as secondary electrons, back-scattered electrons, Auger electrons and X-ray quanta are reflected or scattered.

EDX detector 14 is positioned such as to detect at least a portion of the emitted X-ray. EDX detector 14 is a broadband X-ray detector capable of providing a radiation spectrum that may be analyzed to determine which materials interacted with the electron beam. The inventor used various EDX detectors, such as an EDX detector of Thermo Noran that has Phi-Rho-Z electron probe correction program named PHI-RHO-Z. The inventors also applied other quantitative correction schemes such as the ZAF analysis. Phi-Rho-Z correction program and the ZAF analysis convert X-ray intensity peak areas into chemical values representative of the elemental weight fractions of the elemental constituents of the specimen. These techniques compensate for various phenomena that occur when a sample made of multiple materials is EDX analyzed.

A brief description of an EDX analyzer that used ZAF analysis can also be found at U.S. Pat. No. 5,299,138 of Fiori et al. which is incorporated herein by reference.

Sample 20 is positioned on a stage 22. During the process monitoring a relative movement is introduced between the sample 20 and the primary electron beam 2. This may involve mechanical movement of sample, mechanical movement of other parts of SEM 10 and/or electrical deflection of the beam 2, or a combination of movements and deflection. Typically, the mechanical movement is introduced when a certain target or a certain area are being located, but it may also be introduced while scanning said target or area.

Figure 5A:
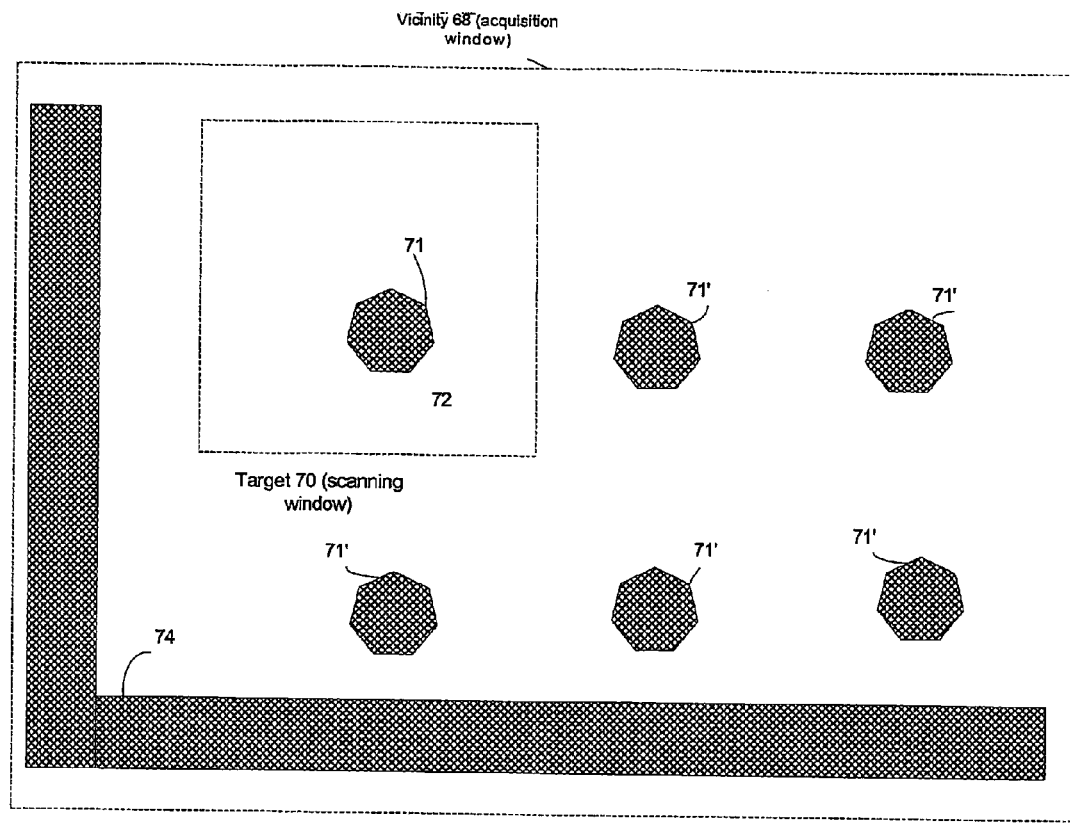
FIGS. 5a-5d illustrate exemplary targets.
Figure 6:
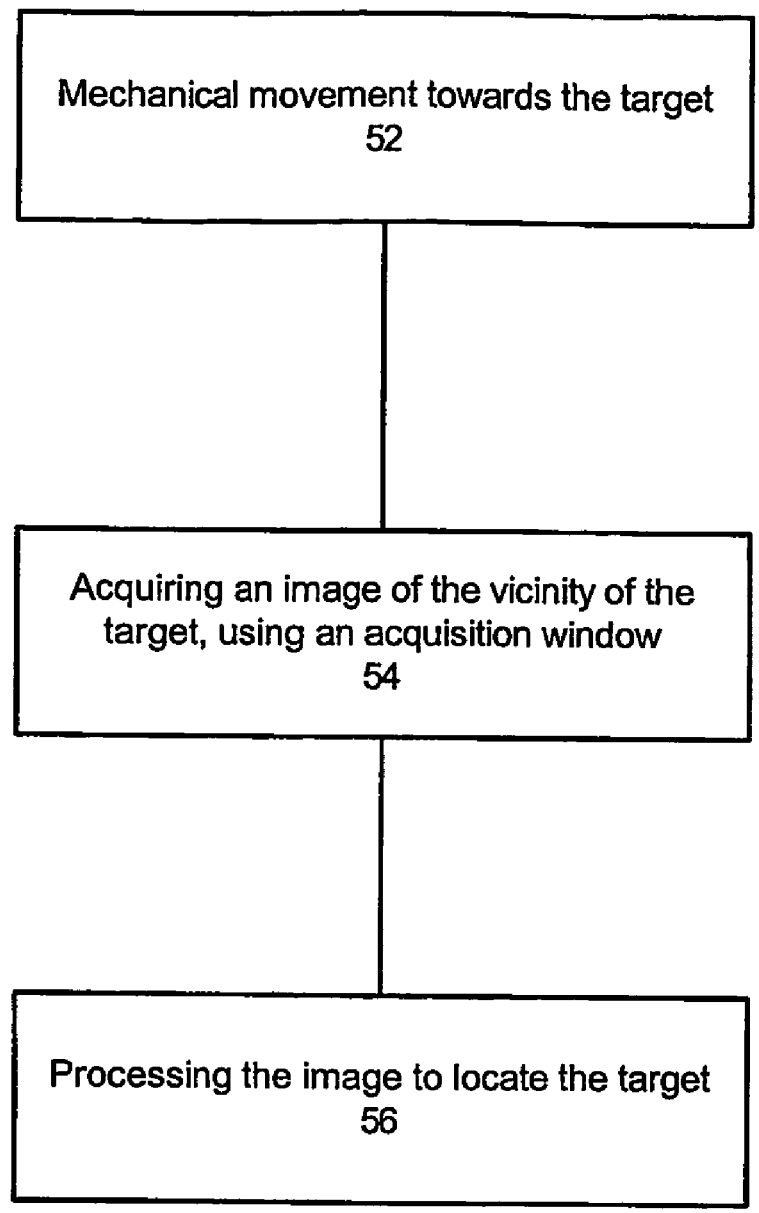
FIG. 6 illustrates a method for locating a target or an area, according to an embodiment of the invention.

When a certain target or area has to be inspected, there is a need to locate that certain target or area. An exemplary locating process is described at FIG. 6. FIG. 6 illustrates a process 50 of locating an area or a target. Process 50 starts at step 52 of optionally mechanical movement towards a vicinity of that certain target or area. Step 52 is followed by step 54 of acquiring an image of said vicinity, usually using a field of view that is derived from mechanical movement inaccuracies. The image is acquired by scanning said vicinity within an acquisition window. FIG. 5a illustrates such a vicinity that includes the target (which in turn includes a via surrounded by oxide), as well as additional vias 71' and an L-shaped conductor 74. Step 54 is followed by step 56 of processing the image to locate the target or area. Step 56 usually includes comparing a target by comparison with a previously acquired target image. Once the certain target or area is located it is scanned with a scanning window that is usually much smaller than the acquisition window. It is noted that the size of the scanning window is usually responsive to signal to noise ratio of the EDX sensor being used for the process monitoring process and/or to the response period of said EDX detector. This is because for a certain size of inspected pattern, the signal from the pattern itself is inversely proportional to the scanned area.

SEM 10 is typically used for implementing various process monitoring methods, such as methods 100-300, but some steps may require other tools, such as an optical inspection tool or Critical Dimension SEM to be used during step 210 of method 200.

SEM 10 may include additional electrodes and anode that are positioned along the path of the beam of charged particles. These may be connected to current meters that may evaluate the intensity of the beam of charged particles, as portions of the beam may interact with these electrodes or electrodes. The beam mal also directed to a special target (formed within the sample) in order to allow beam intensity measurements.

SEM 10 includes a processor 8 that processed the detection signals, and may also control the operation of various parts of SEM 10. Typically, processor 8 has image processing capabilities as well as control capabilities. For example, processor 8 may determine in which manner to process the detected X-ray emission, how to generate a map.

A map generation may involve determining which colors and/or symbols to assign to various void volume ranges, to various flatness value ranges, target thickness ranges, to void depth range and the like.

Figure 3:
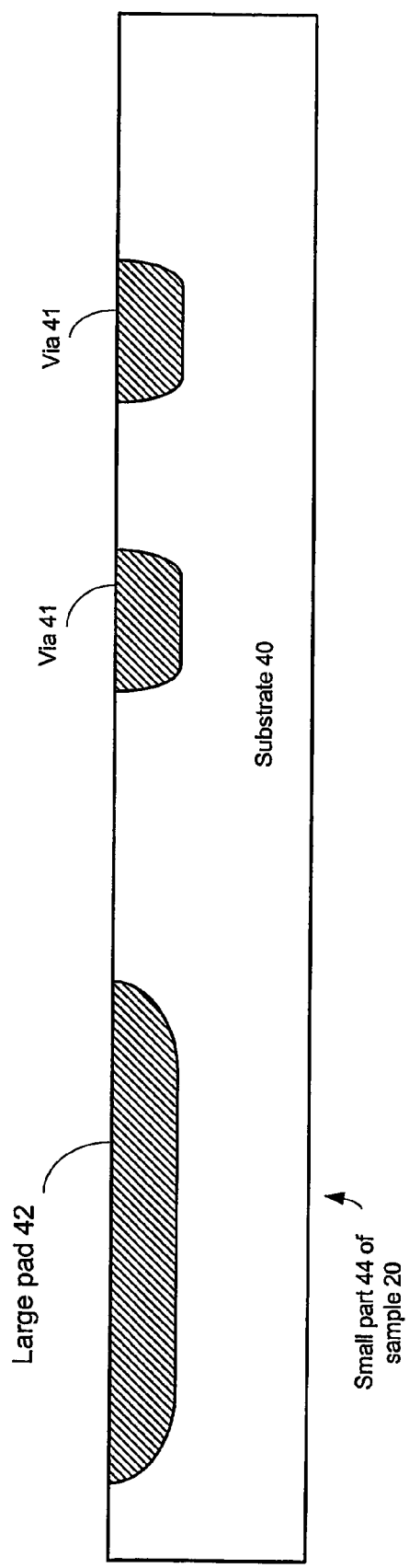
FIG. 3 illustrates a cross section of a small part of a sample.

FIG. 3 illustrates a cross section of a small part 44 of a sample 20. Said small part 44 includes a substrate 40 that surrounds multiple vias 41 as well as a large pad 42, each is surrounded, but not covered by, substrate 40. The large pad and vias (which are illustrated out a scale) are made of conductive material, such as copper. The conductive material is deposited to an etched substrate 40 and then are subjected to access conductive material removal process. 42. It is noted that in many cases an intermediate barrier layer may be manufactured between each of the vias 41 and large pad and between the substrate 40.

The processing may result in voids and/or conductor upper surface deformations. These deformations include erosion, dishing and scratches, and are usually significant when the conductor is large. This may occur when the conductor is a pad or a long conductive line, but is of less significance when the conductor is a small interconnect or via. The term large can be defined in relation to the size of the illuminating spot, in response to the size of other objects such as vias, or in response to the influence of size deformations upon the functionality of the integrated circuit.

Figure 4:
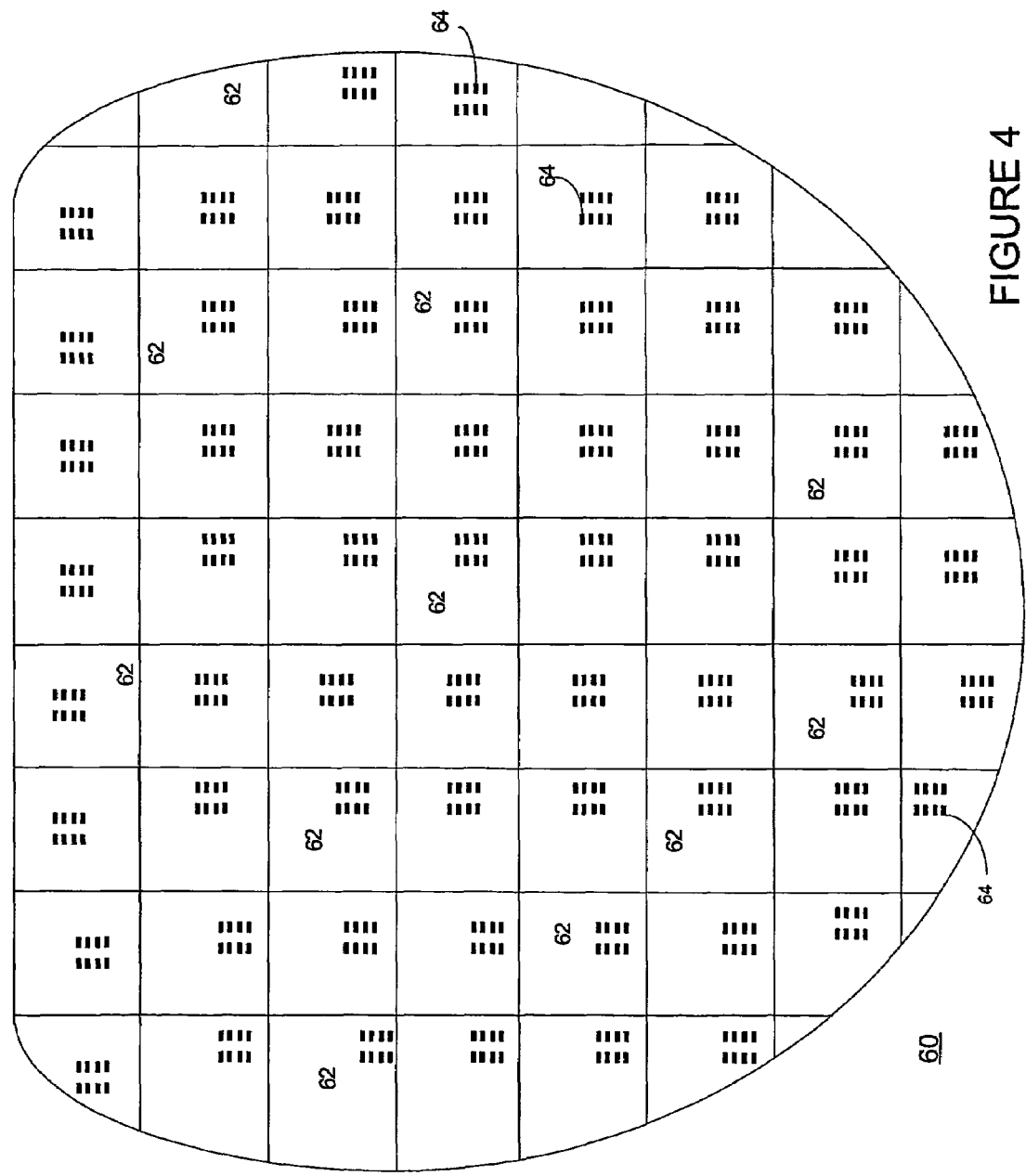
FIG. 4 illustrates a wafer that includes multiple targets.

FIG. 4 illustrates a wafer 60 that includes multiple targets 64. This figure illustrates a wafer 60 that includes multiple dies 62. Each die 62 may include a single target 64 but it usually includes a large amount of targets 64. When many targets are present the process monitoring process may include selecting which targets to evaluate. Some targets may be formed within scribe lines between dies, while others may be formed within the dies themselves. A scanned target or area may include a via that is partially surrounded by silicone oxide, but this is not necessarily so. The inventors also scanned parts of conducting lines, and are aware that other shaped targets may be scanned during to process monitoring process. Typical targets are further illustrated at FIGS. 5a-5d.

In order to provide a comparison between different targets they should include the same composition of materials, and preferably have the same shape. The inventors found that various patterns may be used as targets. For example, a copper via surrounded by oxide may be selected as a target. The selection may be responsive to the manufacturing process characteristics (for example locations that are prone to the creation of voids, large objects that me be subject to dishing, and the like).

Figure 5B:
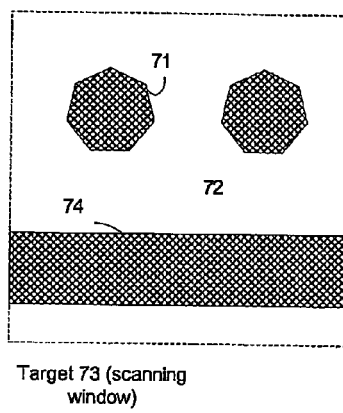
Figure 5C:
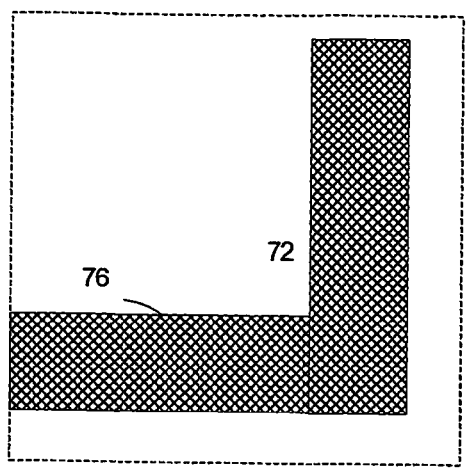
Figure 5D:
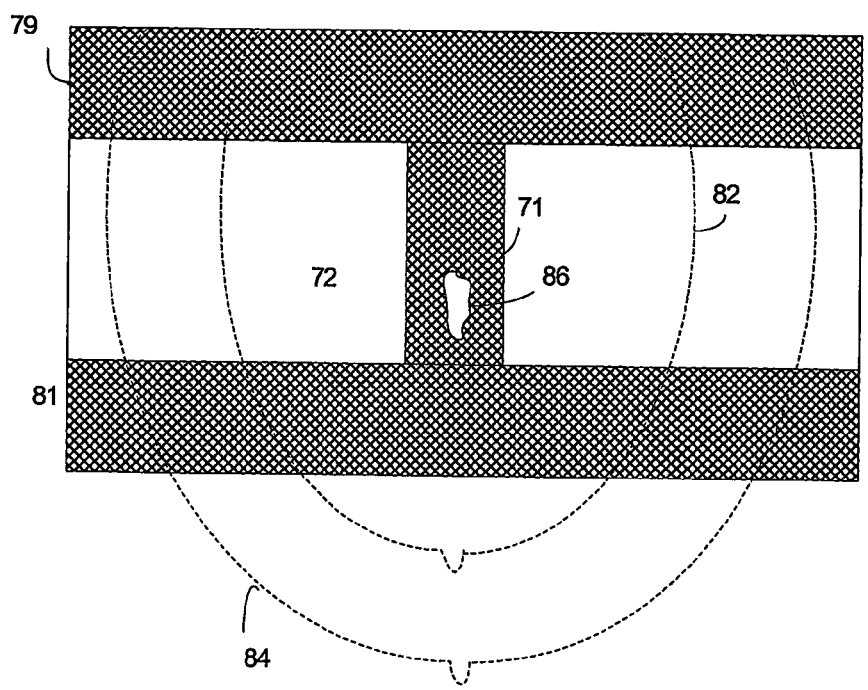

FIGS. 5a-5c illustrates an upper view of various targets 70, 73, 75 and FIG. 5d illustrates a cross sectional view of target 77. Targets 70, 73 and 75 were formed after access copper was removed, while target 77 includes access copper to be later removed. FIG. 5a illustrates target 70 that includes a single copper via 71 surrounded by substrate 72. FIG. 5b illustrates target 73 that includes multiple vias 71 surrounded by substrate 72 as well a part of a conductive line 74. FIG. 5c illustrates target 75 that includes a part 76 of a conductive line that is surrounded by substrate 72. FIG. 5d illustrates target 77 that includes a buried via 71, an upper layer of copper 79 and substrate 72, as well as a possible first portions 82 and an additional portion 84, that are generated by illuminating the target with beams of different energy. The via is connected to the upper layer 79 and to a lower layer 81 of copper. The shape of the first portion and additional portion is responsive to the presence of voids, such as void 86 within via 71.

FIG. 5a also illustrates the vicinity 68 of target 70 that is defined by an acquisition window. The vicinity includes additional vias 71' and an L-shaped conductor. Each of FIGS. 5b-5c illustrates a scanning window.

Figure 7:
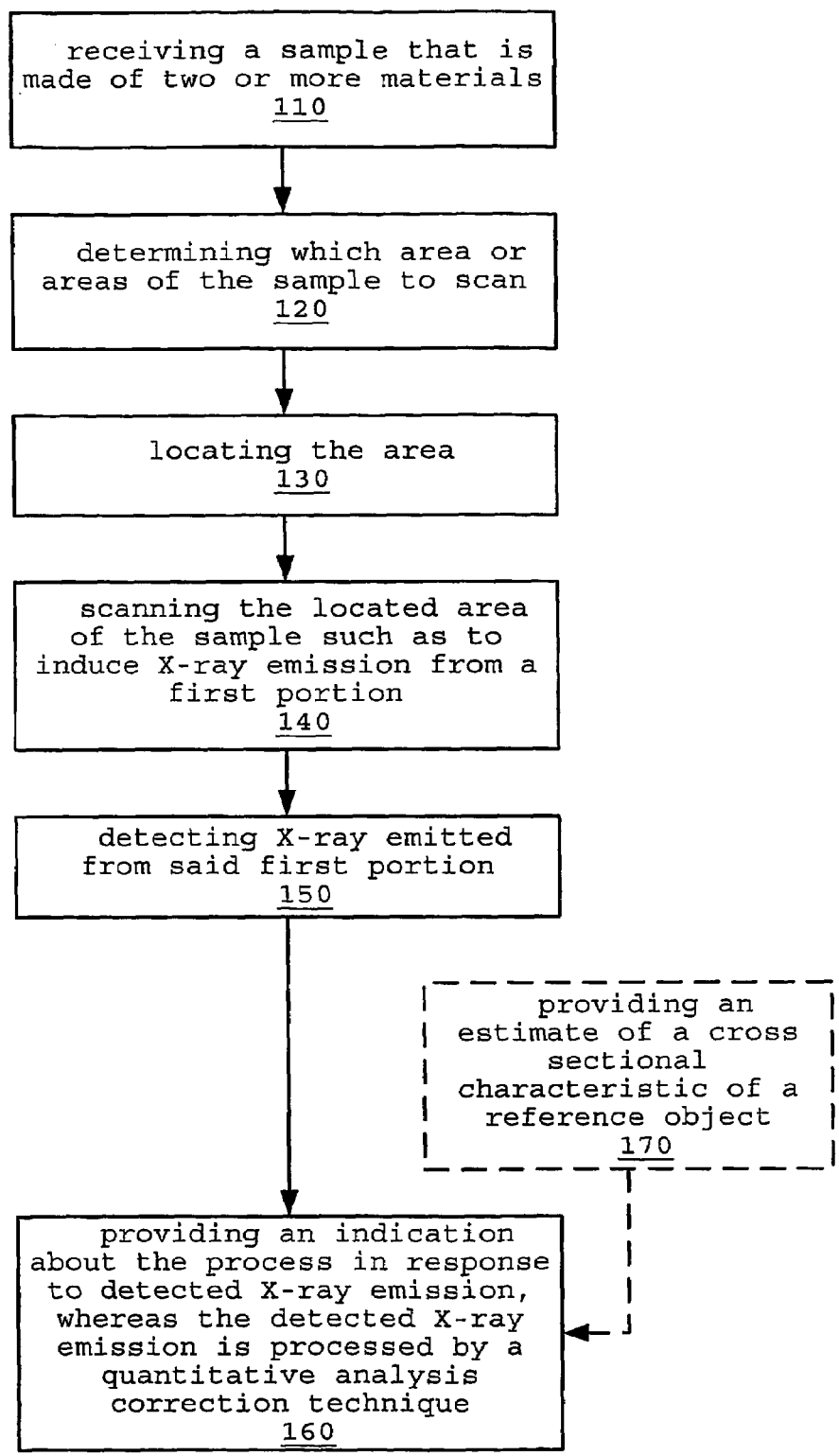
FIGS. 7-9 are flow charts illustrating methods for process monitoring, according to an embodiment of the invention.

FIG. 7 is a flow chart illustration of method 100 for process monitoring. Method 100 starts by step 110 of receiving a sample such as sample 20 that is made of two or more materials. Step 110 is followed by step 120 of determining which area or areas of sample 20 to scan. Usually the sample is a wafer and each area includes targets that in turn may include a copper object (such as vias 71 of FIGS. 5a-5d) that is at least partially surrounded by other materials such as a silicon oxide substrate.

Typically, and especially if a die-to-die comparison is implemented, the same areas are scanned at each die, but this is not necessarily so.

Step 120 is followed by step 130 of locating the area. The location of an area may involve steps 52-56 of FIG. 6, but this is not necessarily so. For example, in some cases a mechanical movement may not be necessary.

Step 130 is followed by step 140 of scanning the located area of the sample such as to induce X-ray emission from a first portion (such as relatively large information volume 5 of FIG. 1 or portions 82 or 84 of FIG. 5d) of the sample.

The shape and size of the first portion is responsive to various characteristics of the sample, as well as those of the beam of charged particles. For example, the penetration of electrons is responsive to the materials from which the vicinity of the interaction target is made of, to the arrangement of materials at that vicinity, as well as the energy of the electrons of the primary beam, incident angle of the beam and the like.

Step 140 is followed by step 150 of detecting X-ray emitted from said first portion. This step may include detecting a portion of said emitted X-rays, as the detection is responsive to the location of the EDX detector, the illuminating path, the sensitivity of the EDX detectors and the like. As previously mentioned, the detection can be executed by multiple detectors. The detectors may be of the same type and characteristics but may differ by their frequency response, as well as their sensitivity.

Step 150 is followed by step 160 of providing an indication about the process. Step 160 involves applying a quantitative analysis correction technique on the detected X-ray emission. Optionally, the estimation may include die-to-die or die-to database comparison. Die to die includes comparing the results of a currently illuminated target to previous results from another target. That inventors found that a comparison of the results of a currently illuminated portion to a previous elimination of another target from the same wafer (or even the same die) is very effective, as various characteristics that alter the emitted X-ray radiation can vary between wafer to wafer and even between die to die. These characteristics may include copper density and the like.

The quantitative analysis correction technique may be a Phi-Rho-Z correction program and/or ZAF analysis that convert X-ray intensity peak areas into chemical values representative of the elemental weight fractions of the elemental constituents of the specimen.

Step 160 may include comparing the results of a current session to an estimated emission. The estimated emission can be responsive to an estimated first portion, and more specifically to estimated materials that may be are included within the first portion, and/or to an estimated arrangement of objects within the first portion.

According to various embodiments of the invention the first portion comprises objects that are made of different materials, such as a conductive object (such as a via, a metal layer conductor connected to the via), a substrate, a barrier layer, and the like. The estimated first portion content may reflect a substantially flawless first portion, but this is not necessarily so. For example, it may reflect a typical first portion. The estimation may be responsive to the design of the inspected sample and/or to previous measurements of other portions of the sample or even other samples. This estimation may include destructive measurements (such as measurements that involve cross sectioning of the sample) or non-destructive measurements of other portions of the sample or other samples.

It is noted the estimation of the first portion may be responsive to one or more parameters that affect the shape or size of the first portion, such as the energy of the primary beam, the angle of incidence and the illuminated sample. The inventors used a Monte Carlo based simulation to estimate emitted X-ray from a sample.

According to an embodiment of the invention step 160 provides an indication that reflects a presence of a void within the first portion. The inventors found that even relatively small voids may be detected. For example, voids that have aggregate volumes of few percents of the via volume were. The depth of voids, as well as their aggregate volume per target can be determined more accurately when the target is illuminated with primary beams of different energies, and even different incidence angles.

According to another aspect of the invention step 160 may provide an indication about the shape of an object positioned in the located area. Such an indication requires multiple measurements of various locations within said object. The various locations may define a grid. Each measurement may reflect the thickness of the object at a certain location. Thus, by measuring the thickness of a certain conductive pad or other large object the method can indicate if the object is flat, deformed, dish-shaped and the like.

According to an embodiment of the invention method 100 may include an optional step 170 of providing an estimate of a characteristic of a reference object. The reference object is typically a filled cavity that is filled with the same conductive material as the inspected object. Step 170 is followed by step 160 in which the indication is also responsive to the estimated characteristic. Typically, the characteristic is a thickness of the reference object.

Step 170 may include measuring a characteristic of the reference object. It may involve multiple measurements at various locations of the reference object, but it may only include a single measurement. The inventors selected to measure the reference object at a location that was selected such as to provide an indication about the thickness of the reference object. The selection may involve estimating where voids do not exist and/or where dishing has a minor effect. For example, given a large reference object, voids are usually located near the edges of such an object. Thus, the inventors selected locations near the center of the object. If there is a chance that the large reference object surface is deformed then additional measurements can be taken to provide a representative parameter of the thickness of the reference object.

Figure 8:
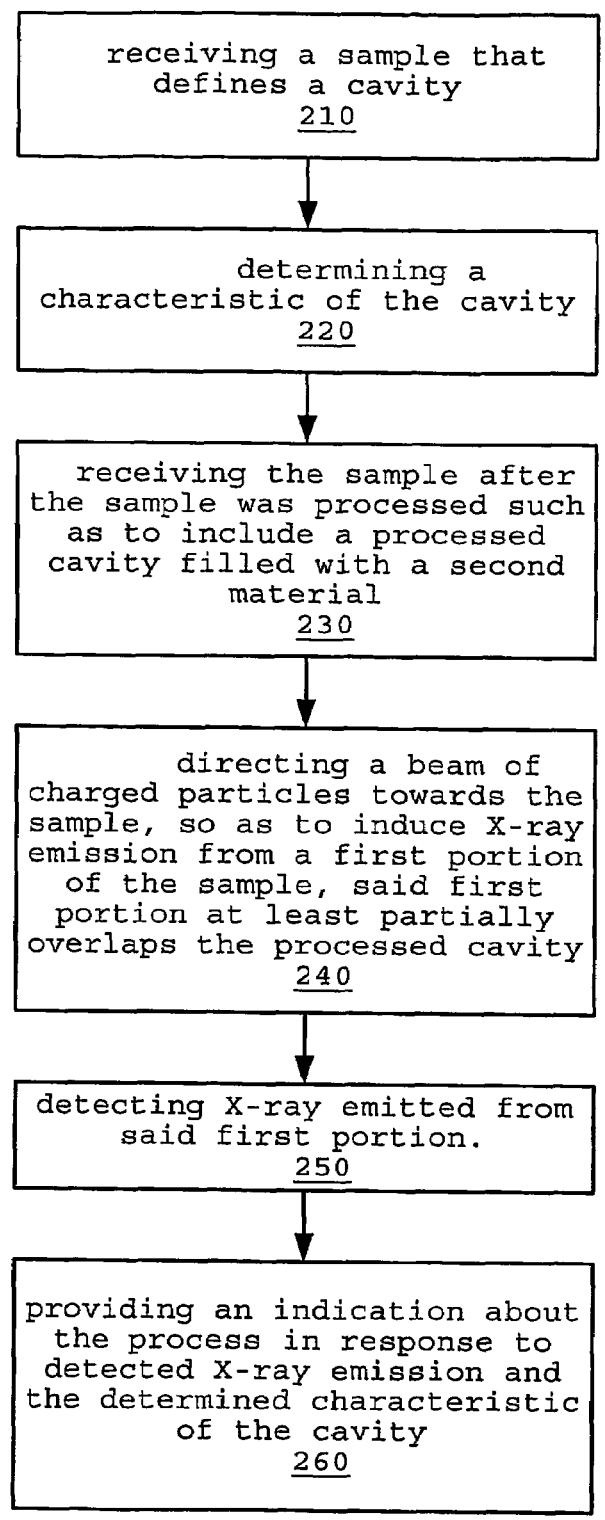

FIG. 8 is a flow chart of method 200 for process monitoring. Method 200 analyzes a sample at multiple stages of the monitored manufacturing process. Method 200 starts by step 210 of receiving a sample that defines a cavity. The sample is made of at least a first material. Typically, sample 20 is an integrated circuit that includes at least a substrate and may also include multiple layers, including conductive layers. The sample may be made of many materials, but at least some of said materials will not influence X-ray emission as they are not included within a first portion that emits X-rays. The cavity can be etched within a substrate to be later filled in with a conductive material such a copper.

Step 210 is followed by step 220 of determining a characteristic of the cavity. The determination may involve determining at least one dimension of the cavity, such as bottom width, top width and even height. The determination may include scanning the cavity with a Critical Dimension SEM (CD-SEM), whereas the scanning may involve normal incidence, as well as tilted incidence. The determination may involve optical measurements, such as those involving reflectometery, and may include estimating the volume of the cavity or its cross section by comparing measurements of the cavity to a bank of previously measured cavities. The determination may include a mathematical analysis of the measurements to provide the determined characteristic. One of these mathematical analysis methods was developed by IBM and involves matching a mathematical formula (usually a polynomial of a certain order) to the measurements.

The determination may be responsive to one or more measurements of the one or more dimensions of the cavity at one or more locations.

Step 220 is followed by a manufacturing step during which the sample is provided to a manufacturing tool to be processed and then provided back to the tool used for x-ray detection (such as SEM 10 of FIG. 2). The processing step includes filling the cavity. It may also include polishing or otherwise removing excess material, but this is not necessarily so. The inventors performed some of their measurements on samples that included a filled cavity and an upper layer of conductive material. In these cases the inventors found that the upper layer usually did not include voids. Nevertheless, without a removal of access material various phenomena such as dishing of the layer below the upper layer are not monitored.

Thus, method 200 includes step 230 of receiving a sample that includes a processed cavity filled with a second material, such as a conductive material and especially such as copper.

Step 230 is followed by step 240 of directing a beam of charged particles towards the sample, so as to induce X-ray emission from a first portion of the sample, said first portion at least partially overlaps the processed cavity. Usually, the first portion includes the processed cavity as well as its surroundings. Once a void is present the first portion is expanded to include more Step 240 is followed by step 250 of detecting X-ray emitted from said first portion.

Step 250 is followed by step 260 of providing an indication about the process in response to detected X-ray emission from the first portion and the determined characteristic of the cavity. According to various embodiments of the invention the indication may reflect the presence of voids within the first portion, or a shape of the filled cavity. It may reflect the thickness of the processed cavity at various locations.

Method 200 was described in relation to a single cavity. It is noted that according to an embodiment of the invention it may be applied to monitor the process in response to multiple processed cavities, each cavity is associated with a different portion. Accordingly, at least steps 230 and 240 repeated for each of the multiple processed cavities. The indication about the process may be responsive to the detected X-ray emission from the portions associated with each cavity and a determined characteristic of at least one cavity. In such a case there are multiple measurements that may be processed in various manners to provide an indication about the process. Each result can stand on its own, but this is not necessarily so and they may be further processed (including statistically processed) to provide various indications.

According to an embodiment of the invention the multiple results are processed to provide a map of the sample indicating X-ray emission measured in response to the detected X-ray emission from the multiple portions of the sample.

According to another aspect of the invention voids characteristics are more accurately defined by performing multiple measurements, while changing various illumination or detection characteristics, such as acceleration voltage, incidence angle, detector location, detector sensitivity and the like. Thus, method 200 may include a further step (not shown, should follow step 250) of changing a characteristic of the beam of charged particles to provide a changed beam and repeating steps 230 and 240 of inducing X-ray emission from a second portion of the sample, said second portion at least partially overlaps the processed cavity; and detecting X-ray emitted from said second portion. Step 260 shall me modified such that the indication about the process is further responsive to detected X-ray emission from the second portion.

According to yet another embodiment of the invention method 200 includes applying a quantitative analysis correction technique on detected X-ray emission to provide the process monitoring.

Figure 9:
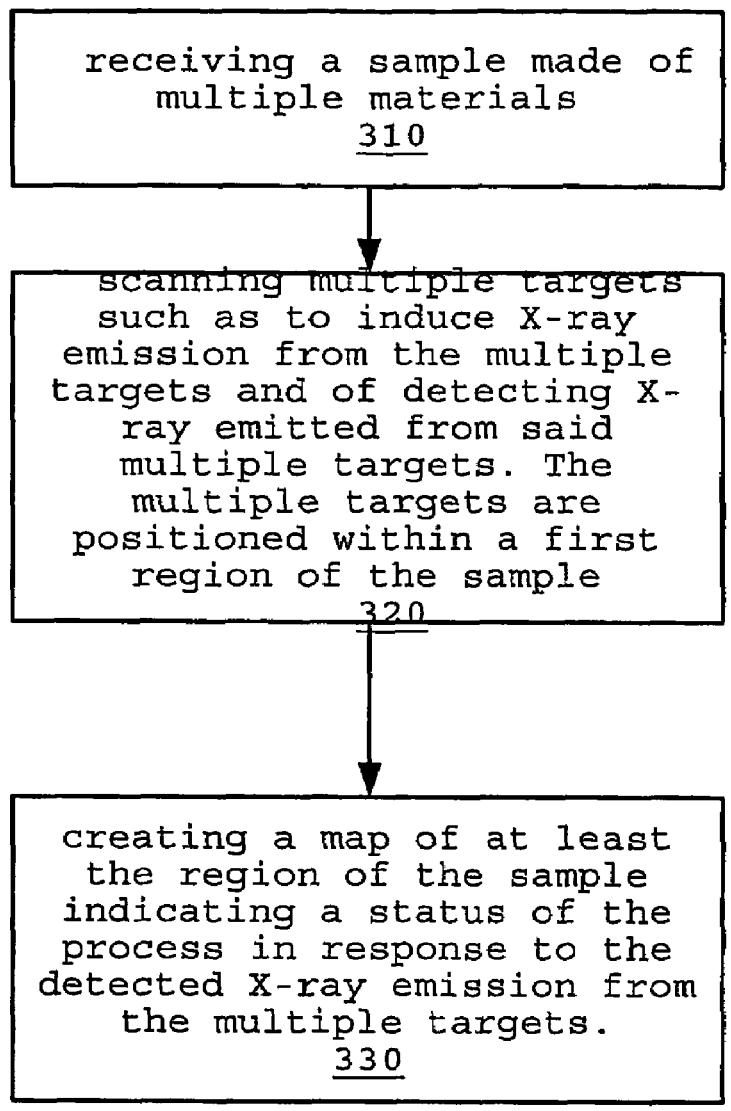

FIG. 9 is a flow chart of method 300 for process monitoring. Method 300 starts by step 310 of receiving a sample made of multiple materials.

Step 310 is followed by step 320 of scanning multiple targets such as to induce X-ray emission from the multiple targets and of detecting X-ray emitted from said multiple targets. The multiple targets are positioned within a first region of the sample. Step 320 may include narrowband or wideband X-ray detection. Exemplary wideband X-ray detection may include EDX detection. Narrowband X-ray detection may include detecting X-ray within a narrowband that usually includes a certain emission line of a selected element, like K-line or L-line of Copper. Narrowband detectors are known in the art and some are described at U.S. patent application Ser. No. 09/990,171 of Nasser-Ghodsi et el.

Each area is illuminated and its radiation is detected before moving to the next area, but simultaneous illumination of multiple targets and corresponding detection may also occur.

Step 320 may include locating the multiple targets. Said location may include the steps of method 50, but this is not necessarily so.

Step 320 is followed by step 330 of creating a map of at least the region of the sample indicating a status of the process in response to the detected X-ray emission from the multiple targets.

Step 330 may include processing measured X-ray emission in response to characteristics of at least two materials of the target. The processing may be Phi-Rho-Z correction program and/or ZAF processing. Said processing may include processing X-ray emission measurements in response to measured intensity of the beam of charged particles.

The map may indicate at least one of the following: the presence of voids within the sample, the depth of the voids, the volume of the voids, deviations in a shape of the target, or dishing phenomena.

Figure 10:
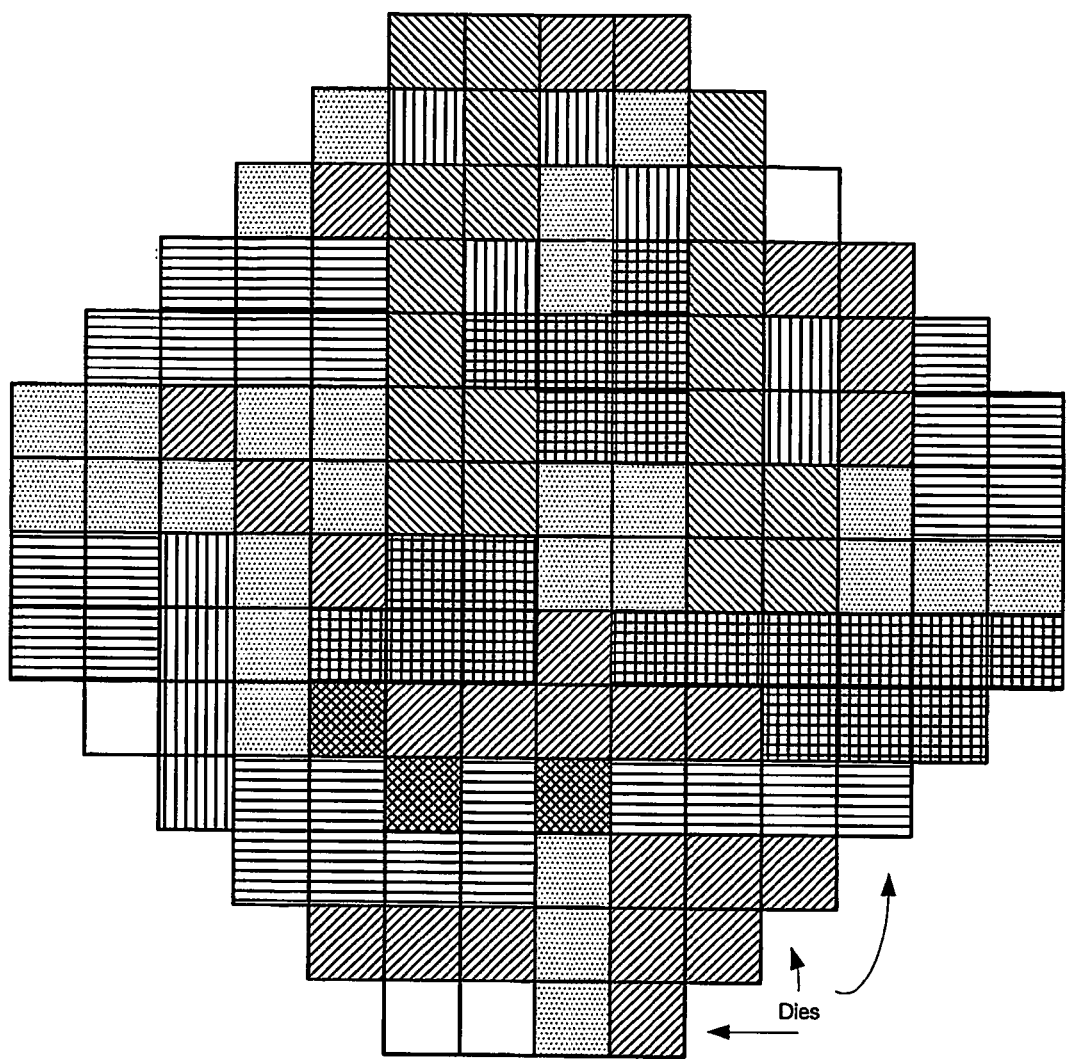
FIG. 10 is an exemplary map of a sample that provides colored indication about void volumes, according to an embodiment of the invention.
Figure 10:
Figure 10:
Figure 10:
Figure 10:
Figure 10:
Figure 10:
Figure 10:

The map may include symbols or colors or a combination of both. Different symbols, colors or a combination of both may be allocated to different void volume ranges, to different void depth ranges, to different target flatness value ranges, to different target thickness value ranges, and the like. Map 400 of FIG. 10 was generated by assigning different colors to different void volumes. FIG. 10 is an exemplary screen of a simulation program that estimated a first portion and especially the radiation emitted from a sample.

According to an aspect of the invention method 300 further includes a step of changing a characteristic of a beam of charged particles that scanned the multiple targets to provide a changed beam and scanning the multiple targets with the changed beam of charged particles, so as to induce additional X-ray emissions from the multiple targets; and detecting the additional X-ray emissions. In this case the indication about the process is further responsive to the additional detected X-ray emissions.

It is noted that a target may be illuminated by a beam and a changed beam before another target is illuminated, but this is not necessarily so. For example, multiple targets can be illuminated by the (unchanged) beam before changing the beam to provide a changed beam.

According to another aspect of the invention once multiple cavities are illuminated, each processed cavity must be located before said illumination. Each processed cavity may be located by acquiring an image of an estimated vicinity of the processed cavity and processing the image to locate the processed cavity. The image is typically acquired by scanning the sample within an acquisition window. Usually, a processed cavity is scanned within a scanning window that is smaller than the acquisition window.

According to yet a further embodiment of the invention the indication about the process is further responsive to a reference parameter, such as a reference parameter that reflects measurements of other processed cavity, or a reference parameter that reflects an estimated detected X-ray emission.

The present invention can be practiced by employing conventional tools, methodology and components. Accordingly, the details of such tools, component and methodology are not set forth herein in detail. In the previous descriptions, numerous specific details are set forth in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method for process monitoring, the method comprising the steps of:
   receiving a sample that defines a cavity, said sample made of at least a first material;
   determining at least one characteristic of the cavity;
   receiving a sample that comprises a processed cavity filled with a second material;
   directing a beam of charged particles towards the sample, so as to induce X-ray emission from a first portion of the sample, said first portion at least partially overlaps the processed cavity;
   detecting X-ray emitted from said first portion; and
   providing an indication about the process in response to detected X-ray emission from the first portion and the at least one determined characteristic of the cavity.

2. The method of claim 1 wherein the step of determining comprises measuring at least one dimension of the cavity at one or more locations.

3. The method of claim 1 wherein the step of determining comprises estimating a volume of the cavity.

4. The method of claim 1 wherein the step of determining comprises scanning a portion of the cavity with a radiation beam.

5. The method of claim 1 wherein the cavity is processed by polishing a previously filled processed cavity.

6. The method of claim 1 wherein the second material is optically oblique.

7. The method of claim 1 wherein the indication reflects the presence of voids within the first portion.

8. The method of claim 1 wherein the indication reflects a shape of the filled cavity.

9. The method of claim 1 wherein the indication reflects the thickness of the processed cavity at various locations.

10. The method of claim 1 wherein the sample defines multiple cavities that are processed to provide multiple processed cavities, each cavity associated with a different portion of the sample.

11. The method of claim 10 wherein the steps of directing a beam and detecting emitted X-rays are repeated for each of the multiple processed cavities.

12. The method of claim 11 wherein the indication about the process is responsive to the detected X-ray emission from the portions associated with each processed cavity and a determined characteristic of at least one cavity.

13. The method of claim 10 further comprising providing a map of the sample indicating X-ray emission measured in response to the detected X-ray emission from the multiple portions of the sample.

14. The method of claim 10 further comprising a step of locating the multiple processed cavities.

15. The method of claim 14 wherein locating a processed cavity comprises acquiring an image of an estimated vicinity of the processed cavity and processing the image to locate the processed cavity.

16. The method of claim 15 wherein the image is acquired by scanning the sample within an acquisition window.

17. The method of claim 16 wherein a processed cavity is scanned within a scanning window that is smaller than the acquisition window.

18. The method of claim 1 wherein the indication is further responsive to a reference parameter.

19. The method of claim 18 wherein the reference parameter is responsive to at least one measurement of at least one other processed cavity.

20. The method of claim 18 wherein the reference parameter is responsive to an estimated X-ray emission.

21. The method of claim 1 further comprising a step of changing a characteristic of the beam of charged particles to provide a changed beam.

22. The method of claim 21 further comprising directing the changed beam towards the sample, so as to induce X-ray emission from a second portion of the sample, said second portion at least partially overlaps the processed cavity; and detecting X-ray emitted from said second portion.

23. The method of claim 22 wherein the indication about the process is further responsive to detected X-ray emission from the second portion.

24. A method for process monitoring, the method comprising the steps of:
receiving a sample comprising at least two materials;
scanning an area of the sample such as to induce X-ray emission from a first portion of the sample;
detecting X-ray emitted from said first portion; and
providing an indication about the process in response to the detected x-ray emission, wherein the step of providing comprises applying a quantitative analysis correction technique on the detected X-ray emission.

25. The method of claim 24 wherein the technique is ZAF analysis.

26. The method of claim 24 wherein the estimated detected radiation is responsive to detected X-ray measurements from at least one other area of the sample.

27. The method of claim 24 wherein the estimation is responsive to an acceleration voltage applied on a beam that scans the area.

28. The method of claim 24 wherein the indication reflects a presence of a void within the first portion.

29. The method of claim 24 wherein the indication reflects a shape of the area.

30. The method of claim 24 further comprising a step of providing an estimate of a characteristic of a reference object and wherein the indication is responsive to said estimated characteristic.

31. The method of claim 30 wherein the characteristic is a thickness of the reference object.

32. The method of claim 30 wherein the characteristic is measured at a location that is selected such as to provide an indication of the characteristic.

33. The method of claim 30 wherein the location is selected in response to a process characteristic.

34. The method of claim 30 wherein the location is positioned substantially at a center the reference object.

35. The method of claim 30 wherein the reference object is large.

36. A system for process monitoring, the system comprising:
means for determining at least one characteristic of a cavity defined by a sample made of at least a first material;
means for directing a beam of charged particles towards the sample so as to induce X-ray emission from a first portion of the sample, said first portion at least partially overlaps a processed cavity; whereas the cavity was processed to provide the processed cavity filled with a second material;
at least one detector for detecting X-ray emitted from said first portion; and
a processor, coupled to the at least one detector, for providing an indication about the process in response to detected X-ray emission from the first portion and the at least one determined characteristic of the cavity.

37. The system of claim 36 wherein the indication reflects the presence of voids within the first portion.

38. The system of claim 36 wherein the indication reflects a shape of the filled cavity.

39. The system of claim 36 wherein the indication reflects the thickness of the processed cavity at various locations.

40. The system of claim 36 wherein the sample defines multiple cavities that are processed to provide multiple processed cavities, whereas each processed cavity is associated with a different portion of the sample.

41. The system of claim 40 wherein the means for directing a beam are further adapted to direct the beam toward each of the multiple processed cavities and to measure the emitted X-ray from each processed cavity.

42. The system of claim 41 wherein the processor is adapted to provide an indication about the process in response to the detected X-ray emission from the portions associated with each processed cavity and a determined characteristic of at least one cavity.

43. The system of claim 41 wherein the processor is further adapted to provide a map of the sample indicating X-ray emission measured in response to the detected X-ray emission from the multiple portions of the sample.

44. The system of claim 41 wherein the system is further adapted to locate the multiple processed cavities.

45. The system of claim 36 wherein the indication is further responsive to a reference parameter.

46. The system of claim 36 further capable of changing a characteristic of the beam of charged particles to provide a changed beam.

47. The system of claim 46 further adapted to direct the changed beam towards the sample, so as to induce X-ray emission from a second portion of the sample, said second portion at least partially overlaps the processed cavity; and to detect X-ray emitted from said second portion.

48. The system of claim 47 wherein the indication about the process is further responsive to detected X-ray emission from the second portion.

49. A system for process monitoring, the system comprising:

means for scanning an area of the sample such as to induce X-ray emission from a first portion of the sample;

at least one detector for detecting X-ray emitted from said first portion; and a processor for applying a quantitative analysis correction technique on detected X-ray emission and in response provide an indication about the process.

50. The system of claim 49 wherein the indication reflects a presence of a void within the first portion.

51. The system of claim 49 wherein the indication reflects a shape of the area.

52. The system of claim 49 further adapted to provide an estimate of a characteristic of a reference object and wherein the indication is responsive to said estimated characteristic.

* * * * *